United States Patent [19]

Hupp et al.

[11] 4,117,021

[45] Sep. 26, 1978

[54] PROCESS FOR REMOVING ORGANIC OXYGEN-CONTAINING IMPURITIES FROM AN ORGANIC COMPOSITION

[75] Inventors: Stephen S. Hupp, Reserve Township, Allegheny County; Edward T. Sabourin, Allison Park; Harold E. Swift, Gibsonia; Roger F. Vogel, Butler, all of Pa.

[73] Assignee: Gulf Research & Development Company, Pittsburgh, Pa.

[21] Appl. No.: 801,050

[22] Filed: May 27, 1977

[51] Int. Cl.$^2$ ............................................. C07C 15/00
[52] U.S. Cl. ........................... 260/669 A; 260/669 R; 260/674 R
[58] Field of Search ............ 260/669 A, 669 R, 674 R

[56] References Cited

U.S. PATENT DOCUMENTS

| Re. 28,137 | 8/1974 | Turner et al. | 260/669 R |
|---|---|---|---|
| 3,476,747 | 11/1969 | Hargis et al. | 260/669 R |
| 3,557,238 | 1/1971 | Cunningham | 260/680 E |
| 3,703,593 | 11/1972 | Turley et al. | 260/669 R |
| 3,963,793 | 6/1976 | Weterings | 260/668 D |
| 3,965,206 | 6/1976 | Montgomery et al. | 260/668 D |
| 3,998,902 | 12/1976 | Foster et al. | 260/669 A |
| 4,044,067 | 8/1977 | Besozzi et al. | 260/669 A |

*Primary Examiner*—Delbert E. Gantz
*Assistant Examiner*—Joseph A. Boska

[57] ABSTRACT

The amount of oxygen-containing impurities in an organic composition is reduced at an elevated temperature by contact with a supported metal oxide. For example, the amount of oxygen-containing organic impurities in a crude stilbene product obtained by oxidatively dehydrocoupling toluene using a solid oxidant is decreased by contact with zinc oxide supported on alumina at an elevated temperature and the resulting purified stilbene product is reacted with ethylene to form styrene.

8 Claims, No Drawings

PROCESS FOR REMOVING ORGANIC OXYGEN-CONTAINING IMPURITIES FROM AN ORGANIC COMPOSITION

FIELD OF THE INVENTION

This invention relates to a method for reducing the amount of oxygen-containing impurities in an organic composition. More particularly, the invention relates to the process for preparing styrene and its derivatives from toluene and its derivatives and to the purification of the intermediate stilbene and its derivatives. In this process toluene or a derivative of toluene is oxidatively dehydrocoupled using a solid oxidant to form a reaction product containing stilbene or a derivative of stilbene and this reaction product is reacted with ethylene over a disproportionation catalyst to form styrene or a derivative of styrene. Since water and any oxygenated organic compounds produced as by-products in the dehydrocoupling reaction will poison the disproportionation catalyst, these compounds are substantially eliminated before the ethenolysis reaction.

DESCRIPTION OF THE PRIOR ART

*Catalysis Reviews*, 3(1), 44(1969) discloses that polar compounds in feed streams to disproportionation catalysts will deactivate the catalysts. Specifically mentioned are water, acetone and methanol.

In U.S. Pat. No. 3,965,206 toluene is converted to styrene in a multi-stage procedure including the oxidative dehydrocoupling of toluene and terminating with the reaction of stilbene and ethylene by olefin metathesis. In this process a stilbene fraction containing some of the polar impurities present in the toluene dehydrocoupling effluent is removed from this reaction mixture. Polar impurities are separated from this stilbene fraction by one of the following specified techniques: by passage through a bed of absorbent material, by fractional crystallization, by solvent extraction, or by reaction in the absence of water with an active metal compound such as sodium metal or disodium stilbene.

SUMMARY OF THE INVENTION

When toluene is oxidatively dehydrocoupled at an elevated temperature with a solid oxidant, the crude reaction product includes unreacted toluene, benzene, bibenzyl, stilbene, water, carbon dioxide and trace amounts of organic oxygenated compounds in which the oxygen is present predominantly as carbonyl and hydroxyl. We have surprisingly discovered that this crude reaction product can be treated for removal of the minute amounts of the organic oxygenated compounds in the presence of certain supported metal oxides if the water present in the crude dehydrocoupling reactor effluent is substantially removed prior to the purification treatment.

The dehydrocoupling of toluene is an oxidative reaction in which the oxygen is supplied by a suitable solid oxidant such as a metal oxide, a non-metal oxide, or a mixture thereof. U.S. Pat. No. 3,476,747 discloses arsenic pentoxide, antimony tetroxide and pentoxide, bismuth trioxide and manganese arsenate as the oxidant for the oxidative dehydrocoupling reaction, U.S. Pat. No. 3,494,956 discloses lead oxide, cadmium oxide and thallium oxide as the oxidant while U.S. Pat. No. 3,965,206 specifies lead oxide, cadmium oxide and bismuth oxide as the oxidant. Any suitable metal oxide, non-metal oxide or mixture of such oxides which can supply oxygen at the elevated temperatures for the oxidative reaction can be used in preparing the crude, stilbene-containing reaction product. The solid oxidant is preferably supported on a suitable support such as fused silica, alumina, a silica-alumina, and the like, or less preferably it can be unsupported.

This oxidative dehydrocoupling reaction is carried out at an elevated temperature, suitably between about 500° C. and about 700° C., preferably between about 550° C. and about 625° C. In carrying out the reaction heated toluene is introduced into the reactor preferably together with steam. Although some water is produced by the oxidative reactions taking place in the reactor, it is preferred that a substantial amount of water be added to the reactor in the form of steam to serve as a diluent and to help control the reaction. The mol ratio of added steam to toluene can suitably be from 0 to about 30, preferably from about 1 to about 15. It is also possible to add molecular oxygen to supplement the oxygen provided by the solid oxidant, but it is preferred to carry out the reaction without using free oxygen. Molecular oxygen can be used in a mol ratio of molecular oxygen to toluene of 0 to about 4, preferably 0 to about 1.

The product stream from this oxidative dehydrocoupling stage includes water as steam, and trace amounts of oxygen-containing containing organic compounds in addition to the hydrocarbon components. These oxygen-containing impurities are primarily aromatic compounds in which the oxygen is present as carbonyl and hydroxyl, with carbonyl predominating. These organic polar compounds will decompose in the presence of the disproportionation catalyst producing, in part, water. Since water causes the rapid deactivation of disproportionation catalysts, the water and the oxygen-containing organic compounds must be substantially eliminated from the feed stream to the ethenolysis reaction.

In accordance with our process the organic portion from the oxidative dehydrocoupling reactor is subjected to a purification treatment in the presence of a suitable metal oxide catalyst to convert the oxygen in these oxygen-containing impurities to water which is readily removable. In carrying out this purification the hot, gaseous stream from the dehydrocoupling reactor is first cooled and the water substantially removed by a suitable technique such as by condensation, by selective absorption, by molecular sieves, by azeotroping, or any other suitable water removing procedure to prevent water inactivation of the metal oxide. This dewatered dehydrocoupling reactor effluent will contain no more than about one weight percent water, preferably no more than about 0.5 percent water. The carbon dioxide in the stream is also removed at this stage. The organic portion of the dehydrocoupling reactor effluent is then reheated for the purification treatment.

Metal oxides which can be used in our purification procedure include the oxides of Group IIb metals including zinc, cadmium and mercury; Group Vb metals including vanadium, niobium and tantalum; Group VIb metals including chromium, molybdenum and tungsten; Group VIIb metals including manganese and rhenium; and oxides of titanium, iron and nickel. These metal oxides are supported on a carrier, preferably alumina. Also useful as supports for these metal oxides are silica, silica-alumina, magnesium aluminate, zeolites, clays, and other materials commonly used as supports in the art. These supports will generally have a surface area of between about 50 and about 350 $M^2/g$.

The supported metal oxide catalyst functions as a purification agent by aiding in the removal of the oxygen from the organic composition undergoing treatment. In preparing these purification agents a compound of the desired metal can be deposited on the support or mixed with the support by any suitable method commonly known in the art for such purpose, such as impregnation from solution, and the like. The resulting material is dried and then heated at an elevated temperature in an air atmosphere. Combinations of two or more metal oxides can also be used. The resultant material which is useful to decrease polar impurities in the dehydrocoupling reactor effluent will contain from about 0.1 to about 50 percent of the metal oxide on the support, preferably from about 2 to about 20 percent.

The supported metal oxide can effect a substantial reduction in the amount of the oxygen-containing organic compounds when used in the purification of the oxidative dehydrocoupling effluent. The amount of the oxygen-containing organic impurities is determined by analyzing for carbonyl content. It is believed that using the carbonyl content as the indicator of the presence of oxygen-containing organic impurities and as a measure of the degree of purification is reliable both because carbonyl in the form of aromatic aldehydes and ketones is considered to be the primary organic oxygen-containing impurity and for the further reason that this primary carbonyl impurity is believed to occur in a generally constant proportion with respect to the other organic, oxygen-containing impurities. We have found that it is desirable to reduce the amount of oxygen-containing compound in this purification step down to 50 parts per million (ppm.) or less measured as carbonyl, preferably down to 35 ppm. or less carbonyl and most preferably down to 20 ppm. or less carbonyl as determined by the following test for measuring trace carbonyl content.

A 0.8 to 5.0 g. sample of the dehydrocoupling effluent (the amount inversely adjusted to the anticipated concentration of carbonyl) is placed in the first of two 25 ml. flasks and 1.0 ml. of a saturated solution of 2,4-dinitrophenylhydrazine (100 ml. of water and 2.0 ml. of hydrochloric acid (sp. gr. 1.19) saturated with 2,4-dinitrophenylhydrazine) is added to both flasks. One drop of hydrochloric acid (sp. gr. 1.19) is added to both flasks with swirling. The flasks are heated at 55° C. in a water bath for 30 minutes with swirling every five minutes. The flasks are removed from the bath and allowed to stand at room temperature (25° C.) for 30 minutes with swirling every five minutes. Five ml. of alcohol potassium hydroxide solution (60 g.KOH/1. of methanol/water solution containing 11.2 percent water) is added to each flask with swirling and allowed to stand for five minutes. Following this each flask is diluted to volume with absolute methanol and mixed. Within 10 minutes of the addition of the alcoholic potassium hydroxide solution a portion of the wine-red colored solution containing the sample is placed in a cuvette and measured for absorbance at 430 m$\mu$ against the prepared blank (second flask). The concentration of carbonyl is determined from a calibration chart prepared from similar solutions containing a known amount of carbonyl and analyzed by the above technique.

Our purification procedure can suitably be carried out at a temperature between about 150° C. and about 600° C. and preferably at a temperature between about 210° C. to about 500° C. Pressure is not a critical factor in the purification reactor. The pressure can conveniently range from about atmospheric to about 3,500 kPa. and most generally will be atmospheric or slightly higher. The crude product stream is passed over the catalyst at a liquid hourly space velocity, LHSV, of between about 0.1 and about 50, preferably between about 0.5 and about 15 for most effective conversion and removal of the oxygenated organic impurity.

The product leaving the purification reactor contains toluene, benzene, stilbene, bibenzyl, a small amount of water and no more than a residual amount of the undesired oxygen-containing organic compound which can be tolerated by the disproportionation catalyst. Since the water in this effluent stream from the purification stage will significantly reduce the activity of the disproportionation catalyst, this water is removed prior to the metathesis reactor. Any conventional means for removing water such as by condensation, selective absorption by molcular sieves, azeotroping, and the like can suitably be used. These various water removal procedures involve a cooling of the product stream. Water is removed at this stage down to an amount of 20 ppm. or less, preferably to an amount of 10 ppm. or less.

This oxidative dehydrocoupling reactor product stream with the water and oxygenated organic compounds substantially removed is now suitable for the ethenolysis reaction. The ethylene can be added to this purified product stream prior to its introduction into the metathesis reactor or the ethylene can be added directly to the reactor. Although one mol of ethylene will react by metathesis with one mol of stilbene to form two mols of styrene, it is preferred that an excess of ethylene be used to help drive the reaction to completion. Therefore, a mol ratio of ethylene to stilbene of between about 1:1 to about 100:1 can suitably be used, but it is preferred that a mol ratio of about 2:1 to about 20:1 be used.

In this olefin metathesis reaction between the stilbene and the ethylene, any olefin disproportionation catalyst can be used. Examples of suitable catalysts include the oxides of tungsten, molybdenum, rhenium, uranium, vanadium, niobium, and tantalum and the sulfides and carbonyls of tungsten and molybdenum. These catalysts are carried on a suitable support such as alumina, silica, silica-alumina, a spinel such as zinc aluminate and magnesium aluminate, alumina-aluminum phosphate, and the like. The disproportionation catalyst can desirably be modified by addition of a suitable compound of an alkali metal, alkaline earth metal, thallium, cuprous copper, silver and the like to control surface acidity. Other metals such as cobalt and nickel can be associated with such catalysts.

The conditions for methathesis depend, in part, on the specific catalyst which is used. These conditions are well known in the art. The temperature for carrying out metathetic reactions is broadly within the range of about 150° C. to about 650° C. and usually it is between about 450° C. to about 650° C. The optimum temperature is generally between about 500° C. and about 600° C. In our process the methathesis reaction is preferably carried out under conditions to maximize the conversion of stilbene to styrene. The pressure in the reactor will generally be about atmospheric pressure for enhanced selectivity.

The product stream from the metathesis reactor will contain toluene, styrene, benzene, ethylene, bibenzyl and minor amounts of stilbene and impurities. This stream is fractionated to recover the ethylene, toluene and bibenzyl for recycle and to recover styrene and benzene as product. The bibenzyl is recycled to the oxidative dehydrocoupling reactor for reaction to stilbene.

Although the above procedure as described provides for the purification of the total product stream from the oxidative dehydrocoupling reactor with only water and carbon dioxide removed and use of this stream in the metathesis reaction, this procedure is not critical. Thus, the crude stream from the dehydrocoupling reactor can be fractionated into various organic fractions and the recovered stilbene-containing fraction can then be treated in accordance with the purification procedure of the present invention.

In carrying out the purification procedure described herein, it may be desirable to add a small amount of free hydrogen to the feed gas stream to enhance the removal of carbonyl and hydroxyl contamination. Such added hydrogen can comprise up to about three volume percent of the feed stream to the purification reactor to accomplish a suitable reduction in analyzed carbonyl content.

DESCRIPTION OF PREFERRED EMBODIMENTS

In the following examples, dehydrocoupled product used as the feed to the purification reactor was the organic portion which had been obtained by dehydrocoupling toluene over bismuth oxide or lead oxide as the oxidant and which had been collected and stored for later use. The purification reactor was a tube about seven-eighths inch (22 mm.) I.D. and about 18 inches (46 cm.) long. The upper portion of the reactor was provided with an external electric heater and an internal bed of quartz chips to function as a preheat zone. Below this was placed 20 ml. of 10–20 mesh supported metal oxide which was centered in the tube above a second layer of quartz particles. The liquid organic fraction was metered into the top of the reactor together with nitrogen gas to serve as a diluent and carrier gas. The vaporized organic fraction and nitrogen gas mixture, heated to reaction temperature, passed downwardly through the catalyst bed. Both trans-stilbene and cis-stilbene, separated by chromatographic analysis and separately reported in the following data, react with ethylene by methathesis to form styrene. The minor biphenyl content, obtained from the chromatographic analysis, is also reported below.

EXAMPLE I

A feed stream comprising 86.6 percent toluene, 1.38 percent benzene, 0.16 percent biphenyl, 0.62 percent cis-stilbene, 5.61 percent bibenzyl and 4.73 percent transstilbene and containing 76 ppm. carbonyl was fed into the reactor at a liquid hourly space velocity of 1.0 together with nitrogen at a gas hourly space velocity at 60. The metal oxide was zinc oxide (five percent zinc) on alumina having a surface area of 208 $M^2/g$. After seven hours of operation at 325° C., the product analyzed 87.7 percent toluene, 1.51 percent benzene, 0.24 percent biphenyl, 0.25 percent cis-stilbene, 6.02 percent bibenzyl, and 3.56 percent trans-stilbene and a carbonyl content of 11 ppm. After continuing this procedure for seven additional hours at an elevated temperature of 350° C., the product analyzed as 86.4 percent toluene, 1.45 percent benzene, 0.24 percent biphenyl, 0.37 percent cis-stilbene, 6.11 percent bibenzyl, 4.71 percent trans-stilbene and 18 ppm. carbonyl.

EXAMPLE 2 the procedure of Example 1 at 350° C. was continued using a new feed which analyzed 91.0 percent toluene, 0.98 percent benzene, 0.10 percent biphenyl, 0.40 percent cis-stilbene, 3.76 percent bibenzyl, 3.09 percent trans-stilbene, and 65 ppm. carbonyl. After operating for seven hours with this new feed, the product stream analyzed 90.7 percent toluene, 0.99 percent benzene, 01.14 percent biphenyl, 0.26 percent cis-stilbene, 4.14 percent bibenzyl, 3.28 percent trans-stilbene and 15 ppm. carbonyl. This purification procedure was continued for seven more hours at 350° C., at which time the product stream analyzed 91.6 percent toluene, 0.98 percent benzene, 0.11 percent biphenyl, 0.23 percent cis-stilbene, 3.69 percent bibenzyl, 3.03 percent trans-stilbene and 17 ppm. carbonyl.

EXAMPLE 3

The procedures of Example 1 were repeated at 350° C. using molybdenum oxide (10 percent Mo) on alumina and a feed stream comprising 89.8 percent toluene, 0.71 percent benzene, 0.07 percent biphenyl, 0.41 percent cis-stilbene, 5.46 percent bibenzyl, 2.85 percent trans-stilbene and 74 ppm. carbonyl. After two hours of operation the product stream analyzed 90.9 percent toluene, 0.76 percent benzene, 0.23 percent biphenyl, 5.55 percent bibenzyl, 2.19 percent trans-stilbene and 7 ppm. carbonyl.

EXAMPLE 4

The procedures of Example 1 were repeated at 350° C. using manganese oxide (5 percent Mn) on alumina and a feed stream comprising 90.7 percent toluene, 0.97 percent benzene, 0.09 percent biphenyl, 0.44 percent cis-stilbene, 4.24 percent bibenzyl, 3.01 percent trans-stilbene, and 69 ppm. carbonyl. After two hours of operation, the product stream analyzed 93.5 percent toluene 1.27 percent benzene, 0.10 percent biphenyl, 0.12 percent cis-stilbene, 2.80 percent bibenzyl, 1.83 percent trans-stilbene and 10 ppm carbonyl.

EXAMPLE 5

The procedures of Example 4 were followed at 350° C. using the same feed stream and nickel oxide (5 percent Ni) on alumina. After two hours, the product stream analyzed 91.4 percent toluene, 1.07 percent benzene, 0.21 percent biphenyl, 0.10 percent cis-stilbene, 4.41 percent bibenzyl, 2.05 percent trans-stilbene and 8 ppm. carbonyl.

EXAMPLE 6

The procedures of Example 1 were repeated at 350° C. using chromium oxide (19 percent chromium oxide) on alumina, a stream of nitrogen at a gas hourly space velocity of 4.0, and a feed comprising 89.8 percent toluene, 0.71 percent benzene, 0.07 percent biphenyl, 0.41 percent cis-stilbene, 5.46 percent bibenzyl, 2.85 percent trans-stilbene, and 74 ppm. carbonyl. After two hours of operation of this purification procedure, the product analyzed 90.0 percent toluene, 0.66 percent benzene, 0.09 percent biphenyl, 0.22 percent cis-stilbene, 5.16 percent bibenzyl, 3.46 percent trans-stilbene and 18 ppm. carbonyl.

EXAMPLE 7

The procedures of Example 6 were followed using the same feed at 350° C. and chromium oxide (5 percent chromium) on alumina. After two hours of operation, the product stream analyzed 90.3 percent toluene, 0.72 percent benzene, 0.13 percent biphenyl, 0.14 percent cis-stilbene, 5.72 percent bibenzyl, 2.73 percent trans-stilbene and 10 ppm. carbonyl.

EXAMPLE 8

The procedures of Example 6 were followed using the same feed at 350° C. and titanium oxide (5 percent titanium) on alumina. After two hours of operation, the product stream analyzed 90.6 percent toluene, 0.78 percent benzene, 0.15 percent biphenyl, 6.13 percent bibenzyl, 1.78 percent trans-stilbene and 17 ppm. carbonyl.

EXAMPLE 9

The procedures of Example 6 were followed utilizing five percent vanadium in the form of the oxide on alumina and a temperature of 350° C. and the same feed. After two hours, the purification process was producing a product which analyzed 90.3 percent toluene, 0.68 percent benzene, 0.16 percent biphenyl, 0.18 percent cis-stilbene, 5.38 percent bibenzyl, 2.88 percent trans-stilbene and 15 ppm. carbonyl.

EXAMPLE 10

The procedures of Example 6 were followed utilizing five percent molybdenum in the form of the oxide on alumina and a temperature of 350° C. and the same feed. After two hours, the purification process was producing a product which analyzed 90.7 percent toluene, 0.78 percent benzene, 0.19 percent biphenyl, 5.96 percent bibenzyl, 1.99 percent trans-stilbene and 8 ppm. carbonyl.

EXAMPLE 11

Example 6 was repeated using the same temperature, feed and procedures. The purification agent was 5 percent iron as iron oxide supported on alumina. After 2 hours the product stream analyzed 90.1 percent toluene, 0.68 percent benzene, 0.13 percent biphenyl, 0.19 percent cis-stilbene, 5.59 percent bibenzyl, 3.01 percent trans-stilbene and 15 ppm. carbonyl.

The following examples demonstrate unsuccessful experiments.

EXAMPLE 12

The procedures of Example 6 were followed using 5 percent tungsten as tungsten oxide on alumina. The product after 1 hour of operation analyzed 91.7 percent toluene, 1.53 percent benzene, 0.10 percent biphenyl, 5.70 percent bibenzyl, 0.56 percent trans-stilbene and 12 ppm. carbonyl. This experiment was unsuccessful because of the unacceptably low yield of transstilbene.

The following experiments described in Examples 13 through 15 are unsuccessful because the final carbonyl content is too high.

EXAMPLE 13

The procedures and conditions of Example 6 were followed using the same feed. The purification agent was 5 percent copper as copper oxide on alumina. The product stream after two hours analyzed 90.7 percent toluene, 0.76 percent benzene, 0.13 percent biphenyl, 0.20 percent cis-stilbene, 5.17 percent bibenzyl, 2.78 percent trans-stilbene and 54 ppm. carbonyl.

EXAMPLE 14

The procedures and conditions of Example 6 were followed using the same feed. The purification agent was 5 percent tin as tin oxide on alumina. The product stream after 2 hours analyzed 90.4 percent toluene, 0.78 percent benzene, 0.13 percent biphenyl, 0.18 percent cis-stilbene, 5.28 percent bibenzyl, 2.75 percent trans-stilbene and 79 ppm. carbonyl.

EXAMPLE 15

The procedures and conditions of Example 4 were repeated using cobalt oxide (5 percent cobalt) supported on alumina. After two hours the product analyzed 90.9 percent toluene, 0.97 benzene, 0.15 percent biphenyl, 0.20 percent cis-stilbene, 4.38 percent bibenzyl, 2.95 percent trans-stilbene and 157 ppm. carbonyl.

EXAMPLE 16

All the conditions of Example 6 were repeated except that 20 ml. of aluminum oxide were used. After two hours the effluent stream analyzed 90.1 percent toluene, 1.12 percent benzene, 0.20 percent biphenyl, 0.14 percent cis-stilbene, 5.88 percent bibenzyl, 1.94 percent trans-stilbene and 45 ppm. carbonyl.

EXAMPLE 17

After toluene was coupled over bismuth oxide, the great bulk of the water was removed, pure trans-stilbene was added to bring its stilbene content to about 10 percent and the remaining water was removed to less than 5 ppm. water in a molecular sieve. This product and ethylene serving as a carrier gas in an ethylene to stilbene mol ratio of 8:1 were passed over 8 percent tungsten on silica at a temperature of 480° C. and a pressure of 30 psig. The composition of the feed was 82.6 percent toluene, 0.88 percent benzene, 0.03 percent ethylbenzene, 0.08 percent styrene, 4.9 percent bibenzyl, 0.46 percent cis-stilbene, 10.3 percent trans-stilbene, and 0.78 percent other components including 96 ppm. carbonyl. The purification treatment was conducted for 4 hours. The products of several runs were mixed together to a product which analyzed 83.3 percent toluene, 0.87 percent benzene, 0.24 percent ethylbenzene, 1.68 percent styrene, 4.80 percent bibenzyl, 1.20 percent cis-stilbene, 6.45 percent transstilbene and 1.36 percent other components. The carbonyl content of this mixed product was 22 ppm.

EXAMPLE 18

After drying the product mixture of Example 17 over molecular sieves, it was passed together with ethylene (8:1 mol ratio of ethylene to stilbene) over an 8 percent tungsten on silica catalyst at a temperature of 480° C. and a pressure of 30 psig. After four hours of ethenolysis the product stream analyzed 82.1 percent toluene, 0.88 percent benzene, 3.30 percent ethylbenzene, 6.75 percent styrene, 4.19 percent bibenzyl, 0.53 percent trans-stilbene, 0.1 percent cis-stilbene, and 2.15 percent other components. It is noted that the product styrene content in this example over the previous example increased from 1.68 percent to 6.75 percent following the carbonyl removal.

In the detailed description above our process is shown to substantially reduce the amount of oxygen-containing organic impurities from crude stilbene prepared by the oxidative dehydrocoupling of toluene. Derivatives of toluene can also be oxidatively dehydrocoupled using a solid oxidant to produce the corresponding stilbene derivatives. Examples of derivatives of toluene which can be oxidatively dehydrocoupled include ortho-, meta- and paraxylene; ortho-, meta- and parachlorotoluene; ortho-, meta- and paracyanotoluene; ortho-, meta- and paranitrotoluene; and the like. The oxygencontaining impurities can also be removed from these stilbene derivatives by the process of the present invention and these stilbene derivatives can then be converted to the corresponding styrene derivatives by metathesis with ethylene. Thus, for example, parachlorotoluene is dehydrocoupled to p,p-dichlorostilbene, and this compound following removal of the oxygencontaining organic impurities is converted by ethenolysis to p-chlorostyrene.

It is to be understood that the above disclosure is by way of specific example and that numerous modifications and variations are available to those of ordinary skill in the art without departing from the true spirit and scope of the invention.

We claim:

1. The process for producing styrene from ethylene and toluene which comprises
    (a) dehydrocoupling toluene in the presence of a solid oxide oxidant at a first temperature of between about 500° C. and about 700° C. to form a gaseous product stream comprising toluene, benzene, bibenzyl, stilbene, a minute amount of aromatic carbonyl and aromatic hydroxyl impurities, carbon dioxide and water,
    (b) substantially reducing the carbon dioxide and the water in said gaseous product stream to a maximum water content of about 1 percent,
    (c) purifying said substantially water-free product stream at a second temperature between about 150° C. and about 700° C. by contact with a catalyst comprising an oxide of titanium, iron, nickel, a Group IIb, Vb, VIb or VIIb metal, or a mixture thereof on a support to reduce the aromatic carbonyl and aromatic hydroxyl impurities to a maximum carbonyl content of 50 ppm.,
    (d) removing a substantial amount of water from the purified product stream,
    (e) contacting the substantially water-free and impurity-free reaction product comprising toluene, benzene, stilbene and bibenzyl with ethylene in the presence of a disproportionation catalyst at a temperature between about 150° C. and about 650° C. whereby stilbene and ethylene react to form styrene, and
    (f) separating styrene from the reaction product.

2. The process for producing styrene from ethylene and toluene in accordance with claim 1 in which said second temperature is between about 210° C. and about 600° C.

3. The process for producing styrene from ethylene and toluene in accordance with claim 1 in which from about 0.1 to about 50 weight percent of the said catalyst is on the support.

4. The process for producing styrene from ethylene and toluene in accordance with claim 1 in which the support is alumina.

5. The process for producing styrene from ethylene and toluene in accordance with claim 1 in which the water content of said gaseous product stream is a maximum of about 0.5 percent.

6. The process for producing styrene from ethylene and toluene in accordance with claim 1 in which the carbonyl content of the purified product stream is a maximum of about 35 ppm.

7. The process for producing styrene from ethylene and toluene in accordance with claim 1 in which the carbonyl content is the purified product stream is a maximum of about 20 ppm.

8. The process for producing styrene from ethylene and toluene in accordance with claim 1 in which the water is removed from the purified product stream to a maximum of about 20 ppm.